United States Patent
Dey et al.

(10) Patent No.: US 12,340,886 B2
(45) Date of Patent: *Jun. 24, 2025

(54) METHODS AND SYSTEMS FOR SELECTING A MACHINE LEARNING ALGORITHM

(71) Applicant: Express Scripts Strategic Development, Inc., St. Louis, MO (US)

(72) Inventors: Sudipto Dey, Parsippany, NJ (US); Camille Patel, Baie Durfe (CA); Pulla Reddy P. Yeduru, Leander, TX (US); Robert A. Seyss, Lafayette, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/514,181

(22) Filed: Nov. 20, 2023

(65) Prior Publication Data

US 2024/0087709 A1 Mar. 14, 2024

Related U.S. Application Data

(63) Continuation of application No. 17/994,442, filed on Nov. 28, 2022, now Pat. No. 11,848,086, which is a
(Continued)

(51) Int. Cl.
*G16H 20/10* (2018.01)
*G06N 20/20* (2019.01)
*G16H 50/70* (2018.01)

(52) U.S. Cl.
CPC .......... *G16H 20/10* (2018.01); *G06N 20/20* (2019.01); *G16H 50/70* (2018.01)

(58) Field of Classification Search
CPC ........ G16H 20/10; G16H 50/70; G16H 70/40; G16H 50/20; G16H 40/20; G06N 20/20; G06N 20/00
See application file for complete search history.

(56) References Cited

U.S. PATENT DOCUMENTS

| | | | |
|---|---|---|---|
| 6,658,396 B1 * | 12/2003 | Tang | G16H 20/10 706/17 |
| 10,593,425 B1 | 3/2020 | Truscott | |

(Continued)

OTHER PUBLICATIONS

Lim, C., Kirikoshi, T. Predicting the effects of physician-directed promotion on prescription yield and sales uptake using neural networks. J Target Meas Anal Mar. 13, 156-167 (2005) (Year: 2005).*

(Continued)

*Primary Examiner* — Sheetal R Paulson
(74) *Attorney, Agent, or Firm* — Miller Johnson (57) ABSTRACT

Methods and systems for selecting a machine learning algorithm are described. In one embodiment, one or more factors to be used by a machine learning algorithm in predicting a value of a required pharmacy element of a prescription are identified, the machine learning algorithm is trained to predict the value of the required pharmacy element using a first subset of previously received prescriptions, a success rates for the machine learning algorithm at predicting respective known values of respective known required pharmacy elements for each of a second subset of the previously received prescriptions are determined, and the machine learning algorithm predicts the value of the required pharmacy element of the prescription for a first predetermined period.

20 Claims, 5 Drawing Sheets

Related U.S. Application Data continuation of application No. 16/272,090, filed on Feb. 11, 2019, now Pat. No. 11,515,022.

(56) References Cited

U.S. PATENT DOCUMENTS

| | | |
|---|---|---|
| 2005/0228766 A1 | 10/2005 | Roberts |
| 2005/0240544 A1 | 10/2005 | Kil |
| 2011/0213625 A1 * | 9/2011 | Joao |
| 2016/0055313 A1 * | 2/2016 | Sellars .................. G16H 20/10 705/2 |
| 2018/0075220 A1 | 3/2018 | Hill, Sr. |
| 2019/0019061 A1 | 1/2019 | Trenholm |
| 2019/0080416 A1 | 3/2019 | Smith |
| 2020/0027539 A1 | 1/2020 | Xie |

OTHER PUBLICATIONS

Lim, Chee Woo, et al.—Predicting the effects of physician-directed promotion on prescription yield and sales uptake using neural networks, Journal of Targeting, Measurement and Analysis for Marketing 13.2: 156-167. Palgrave Macmillan. (Feb. 2005) (Year: 2005).

\* cited by examiner

METHODS AND SYSTEMS FOR SELECTING A MACHINE LEARNING ALGORITHM

CROSS REFERENCE TO RELATED APPLICATIONS

This application is a continuation of U.S. application Ser. No. 17/994,442, which was filed Nov. 28, 2022, which is a continuation of U.S. application Ser. No. 16/272,090, which was filed Feb. 11, 2019. The entire disclosure of said applications are incorporated herein by reference.

FIELD

The present disclosure relates generally to the technical field of automatic prescription processing using machine learning. In a specific example, the present disclosure may relate to selecting a machine learning algorithm to predict required pharmacy element values of a prescription.

BACKGROUND

Doctors still commonly use facsimile ("fax" or "faxes") as a communication medium to prescribe prescription drugs. When a facsimile prescription is received by a pharmacy, a pharmacy technician must manually enter prescription data into a computer because the faxes are typically handwritten and not readable by optical character recognition. This data entry process takes a significant amount of time and leads to inefficiencies. Adding to the inefficiencies, a pharmacist must manually verify the prescription data. Together, the data entry and pharmacist verification takes approximately 25 minutes. As such, there is a continuing need to remove these inefficiencies from a prescription filling process. For example, the present invention seeks to mitigate these inefficiencies by a computer filling data values using the most accurate machine learning algorithm.

DETAILED DESCRIPTION

Figure 1:
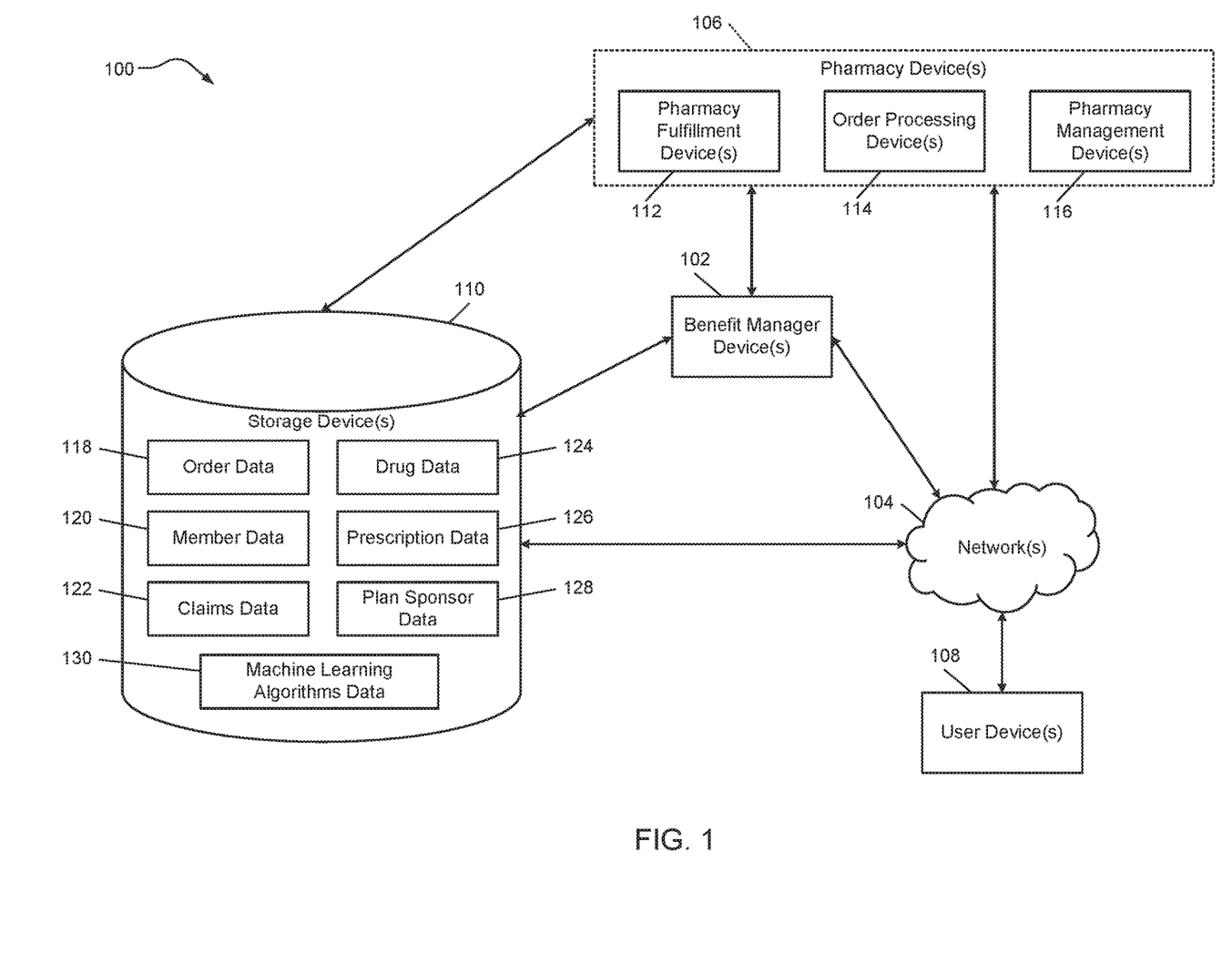
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

In some embodiments, the benefit manager device 102 can include a server, supercomputer, or other computing device configured to implement artificial intelligence algorithms, such as Random Forest, K-Neighbor, Gaussian Naive Bayes, or Stochastic Gradient Descent ("SGD"). In some embodiments, the benefit manager device 102 can include a group of computers, such as a neural network configured to implement artificial intelligence machine learning algorithms.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. In an example embodiment, a doctor or an assistant on behalf of the doctor can upload a prescription to the PBM (e.g. by transmitting a facsimile communication over the network 104). A technician can enter information related to the prescription into the pharmacy device 106 or request the benefit manager device 102 or the pharmacy device 106 to predict some or all values of required pharmacy elements (RPEs) related to the prescription using one of multiple machine learning algorithms. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device 108, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, plan sponsor data 128, and/or machine learning algorithm data 130. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/ or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Furthermore, the machine learning algorithms data 130 can include code or instructions necessary to implement each of multiple machine learning algorithms. The code or instructions can be implemented by one or more processors of the benefit manager device 102 or the pharmacy device 106. Each of the multiple machine learning algorithms can make a prediction for a particular prescription (e.g. a prescription received via fax) based on one or more predetermined factors (e.g. patient age, patient gender, prescribed drug, patient medical conditions), a prediction process that can be performed each time a faxed prescription is received. Each of the multiple machine learning algorithms can include code or instructions to learn from a training dataset, as would be understood by one having ordinary skill in the art. Each of the multiple algorithms can change or adapt the code or instructions based on learning from the training dataset and make predictions according to the changed code or instructions. According to an exemplary embodiment, the multiple machine learning algorithms can include the Random Forest machine learning algorithm, the K-Neighbor machine learning algorithm, the Gaussian Naive Bayes machine learning algorithm, and the SGD machine learning algorithm. In addition, each of the multiple machine learning algorithms can generate confidence values when making a prediction. According to an exemplary embodiment, a confidence value can be a statistical value generated by running statistical analysis on the predictions, and the confidence level can be used to gauge how likely the predictions are to being accurate.

In some embodiments, each of the multiple machine learning algorithms can make a prediction as to RPE values, such as drug quantity (e.g. how many pills per prescription), number of days in a supply, number of refills authorized by a prescribing doctor, and instructions on taking the prescription. By predicting the RPE values, each of the machine learning algorithms can auto-populate values in a prescription form with the predicted values, thereby saving time for a pharmacist or a pharmacist technician in filling a prescription. Other RPEs that can be predicted by each of the multiple machine learning algorithms can include drug price and co-pay amounts.

Each of the multiple machine learning algorithms can make predictions as to RPE values for a prescription using predetermined factors, such as patient age, patient gender, which drug has been prescribed, and medical conditions. Different factors can be used to make RPE value predictions, and the factors and number of factors used to make RPE value predictions can depend on which predetermined factors best lead to prediction accuracy. Each of the multiple machine learning algorithms can learn and improve prediction success using a training dataset by factoring all or some of the predetermined factors listed above. Furthermore, after learning from the training dataset, each of the multiple machine learning algorithms can make predictions for a particular prescription based on all or some of the factors.

Figure 2:
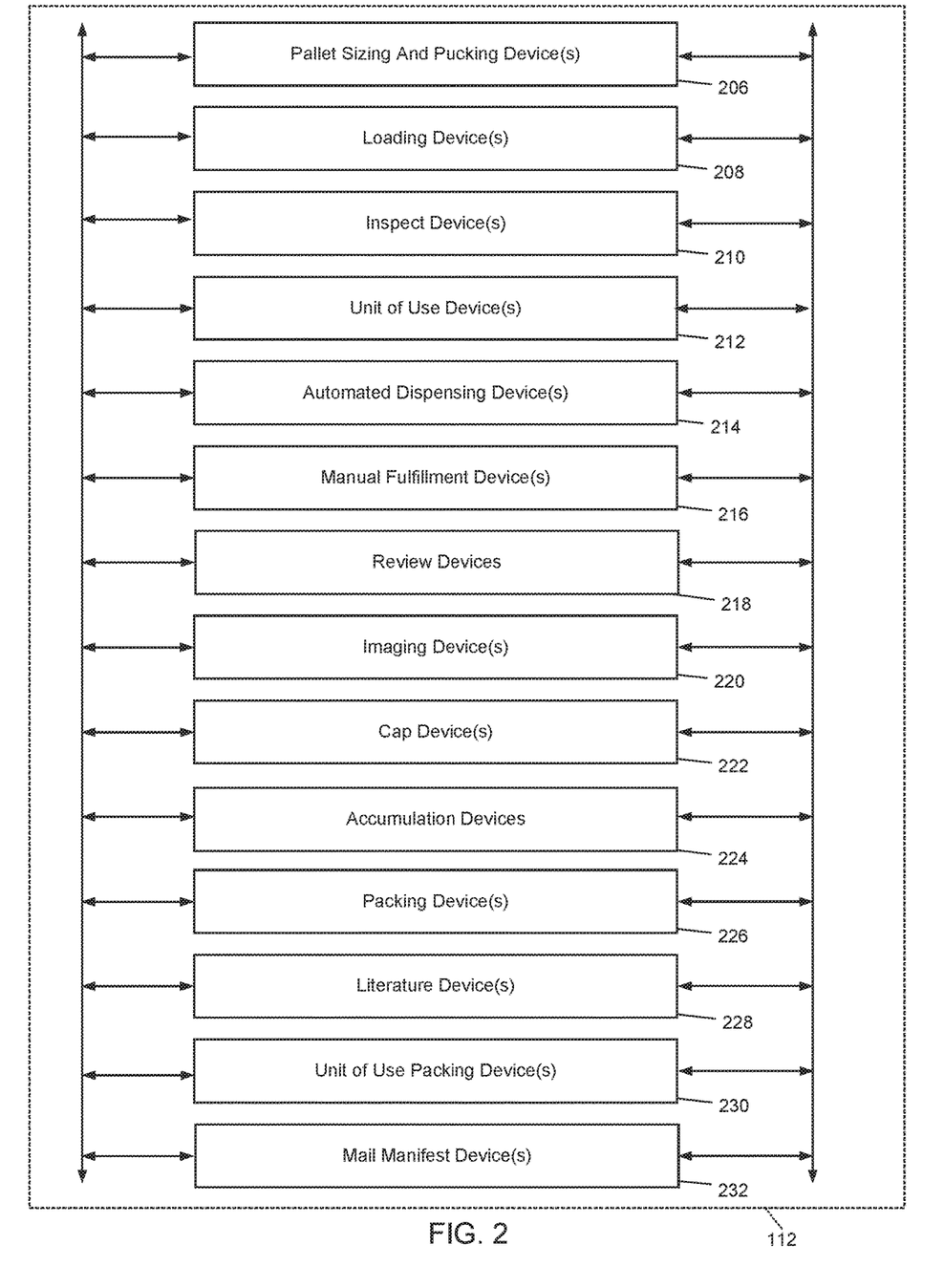
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
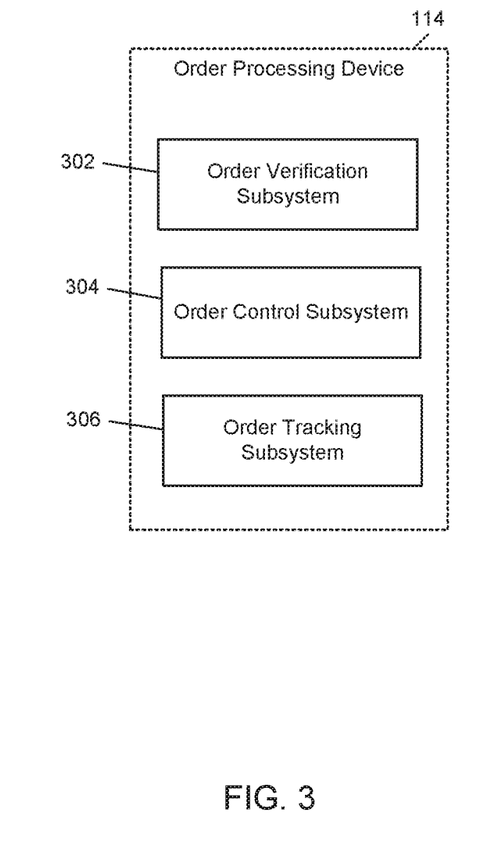
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order related components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 4:
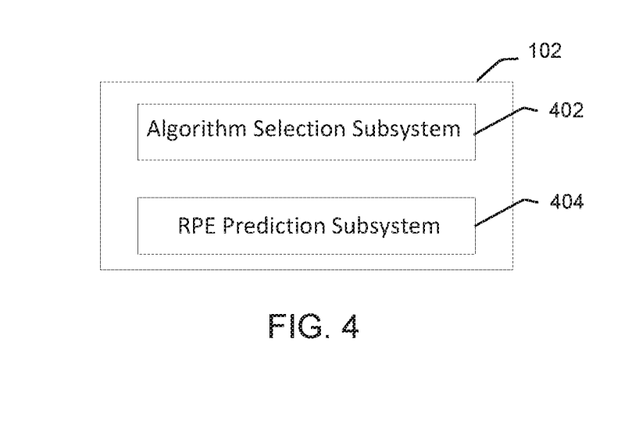
FIG. 4 is a block diagram of an example benefit manager device that may be deployed within the system of FIG. 1, according to an example embodiment.

FIG. 4 illustrates the benefit manager device 102, according to an example embodiment. The benefit manager device 102 may be deployed in the system 100, or may otherwise be used. The benefit manager device 102 may include a machine learning algorithm selection subsystem 402 and an RPE prediction subsystem 404.

According to an exemplary embodiment, the machine learning algorithm selection subsystem 402 can periodically determine which of the multiple machine learning algorithms is the most accurate on a dataset. For example, every Sunday evening, the machine learning algorithm selection subsystem 402 can gather records involving prescription claims (e.g. the claims data 114); however, the machine learning algorithm selection subsystem 402 can perform machine learning algorithm selection other days or times (e.g. once a month on the first of the month, once a day at midnight, etc.).

After gathering the records, the machine learning algorithm selection subsystem 402 can select a first of the multiple machine learning algorithms and train the first of the multiple machine learning algorithms using a predetermined percentage of the gathered records (e.g. 80% of the records). According to an exemplary embodiment, training the first of the multiple machine learning algorithms can include the first of the multiple machine learning algorithms analyzing each record to determine the known RPE values and a relationship between the known RPE values and predetermined factors (e.g. age, prescribed drug, etc.). However, training the first of the multiple machine learning algorithms can include additional processes.

After training, the machine learning algorithm selection subsystem 402 can implement the first of the multiple machine learning algorithms, as trained, on the remainder of the gathered records (e.g. the remaining 20% of the records) to determine a success rate of the first of the multiple machine learning algorithms at predicting RPE values for the remainder of the gathered records. The success rate can be a percentage value indicating how often the first of the multiple machine learning algorithms correctly predicted RPE values for an individual prescription of the remainder of the gathered records. The success rate can also measure a percentage value indicating how often the first of the multiple machine learning algorithms predicted any RPE value (e.g. three RPEs can exist per prescription).

The machine learning algorithm selection subsystem 402 can repeat the process described above using a second of the multiple machine learning algorithms, namely the machine learning algorithm selection subsystem 402 can train the second of the multiple machine learning algorithms using the predetermined percentage of the gathered records, the machine learning algorithm selection subsystem 402 can implement the second of the multiple machine learning algorithms to predict RPE values on the remainder of the gathered records, and the machine learning algorithm selection subsystem 402 can determine the success rate of the second of the multiple machine learning algorithms. This process repeats until the machine learning algorithm selection subsystem 402 determines the success rate for each of the multiple machine learning algorithms. Finally, the machine learning algorithm having the highest success rate is chosen and passed to the RPE prediction subsystem 404.

In some embodiments, the machine learning algorithm selection subsystem 402 can only make predictions when a confidence value is above a threshold (e.g. 80%, 90%, etc.). In addition, the RPE prediction subsystem 404 may only auto-populate predictions having a confidence value over the threshold. Furthermore, predictions having a confidence value below the threshold can be excluded in calculating the success rate, or a prediction having a confidence level below the threshold can be counted as a failure in calculating the success rate.

The process of selecting a machine learning algorithm can repeat periodically (e.g. once a week) using the original dataset and any new data generated between a first iteration of the machine learning algorithms selection process and a second iteration of the machine learning algorithm selection process. For example, the first iteration may use three years of prescription data, and the second iteration may use three years and one week of prescription data, if the machine learning selection process is performed weekly.

After the machine learning algorithm selection subsystem 402 determines which of the multiple machine learning algorithms has the highest success rate for a given dataset, the RPE prediction subsystem 404 can use the machine learning algorithm of the multiple machine learning algorithms having the highest success rate in predicting future RPE values for a given period (e.g. one week). For example, in a first week, the RPE prediction subsystem 404 can predict RPE values using Random Forest, and in a second week, the RPE prediction subsystem 404 can predict RPE values using K-Neighbor.

In some embodiments, the modules of the RPE prediction subsystem 404 may be distributed so that some modules are deployed in the benefit manager device 102 and some modules are deployed in the pharmacy device 106. In one embodiment, the modules are deployed in memory and executed by a processor coupled to the memory.

Figure 5:
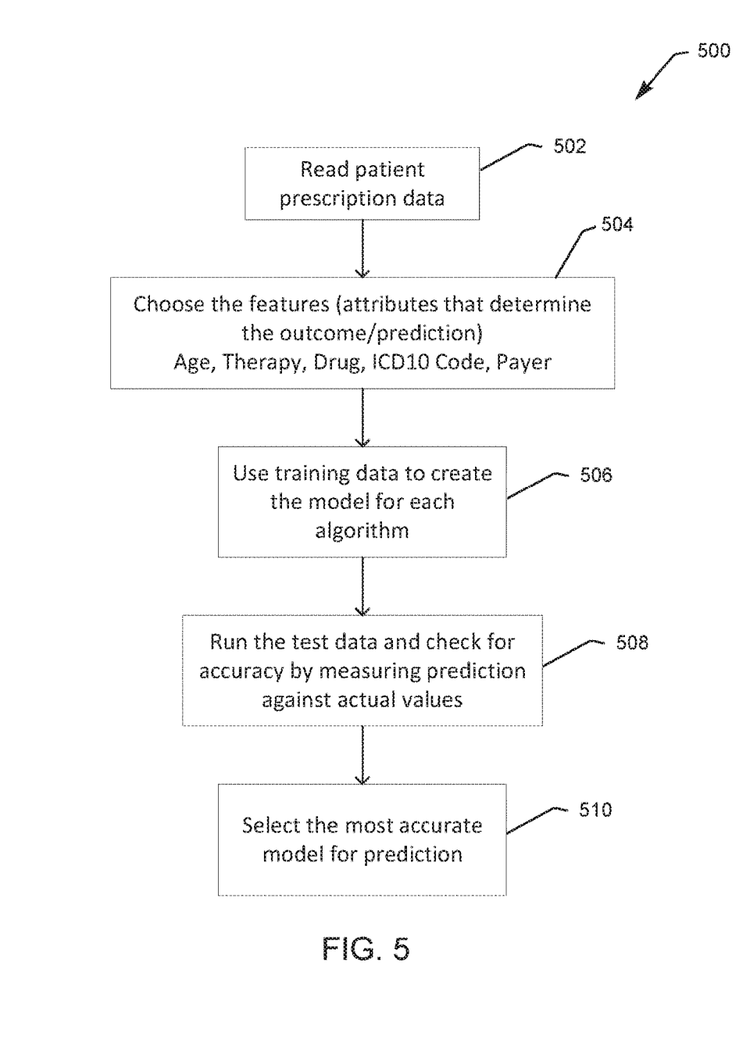
FIG. 5 is a block diagram of a flowchart illustrating methods for selecting a machine learning algorithm for predicting required pharmacy element values in a prescription, according to an example embodiment.

FIG. 5 illustrates a method 500 for selecting one of a multiple machine learning algorithms according to an example embodiment. The method 500 may be performed by the benefit manager device 102, partially by the benefit manager device 102 and partially by the pharmacy device 106, or may be otherwise performed. For the sake of simplicity, the benefit manager device 102 will be described as performing the steps of the method 500, but the embodiments described herein are not so limited.

According to an exemplary embodiment, the benefit manager device 102 can read patient prescription data in step 502. In some embodiments, the patient prescription data read in step 502 can be limited to patient prescription data received through facsimile.

Subsequently, the benefit manager device 102 can choose or reference factors that determine how a machine learning algorithm will predict RPE values in step 504. In some embodiments, the factors can include patient age, drug therapy, prescribed drug, ICD 1 O code, and payer. According to an exemplary embodiment, the chosen features will apply to all machine learning algorithms tested. In some embodiments, the factors are predetermined.

In step 506, the benefit manager device 102 can determine a training dataset to create a model for a first of a multiple machine learning algorithms. The first of the multiple machine learning algorithms can ingest the training dataset and learn from the training dataset, as would be understood to one having skill in the art. In some embodiments, the training dataset can include a subset of the patient prescription data read in step 502 (e.g. 80% of the patient prescription data). In some embodiments, all of the multiple machine learning algorithms can ingest the training dataset and learn from the training dataset substantially simultaneously in step 506.

In step 508, the benefit manager device 102 can apply the first of the multiple machine learning algorithms, as trained, to a test dataset. Furthermore, the benefit manager device 102 can measure prediction success by determining whether the first of the multiple machine learning algorithms correctly predicted an actual RPE value in the test dataset. In some embodiments, the test dataset is a remainder of the pharmaceutical claims data not included in the training dataset (e.g. the remaining 20% of faxed prescription records). In some embodiments, all of the multiple machine learning algorithms can be applied to the test dataset and measure prediction success substantially simultaneously in step 508. Measuring prediction success can include calculating a success rate.

Although not illustrated, the benefit manager device 102 can perform steps 506 and 508 for each of the multiple machine learning algorithms. In other words, steps 506 and 508 can repeat until each of the multiple machine learning algorithms has been trained and tested for accuracy.

Finally, in step 510, the benefit manager device 102 can compare success rates for each of the multiple machine learning algorithms to determine which of the multiple machine learning algorithms had the highest success rate in predicting RPE values. Furthermore, the benefit manager device 102 sets the one of the multiple machine learning algorithms having the highest success rate as the machine learning algorithm to use in future predictions for a specific time period. According to some embodiments, the method 500 can be performed periodically (e.g. once a week, once a month, daily) to dynamically select a machine learning algorithm for prediction purposes.

Figure 6:
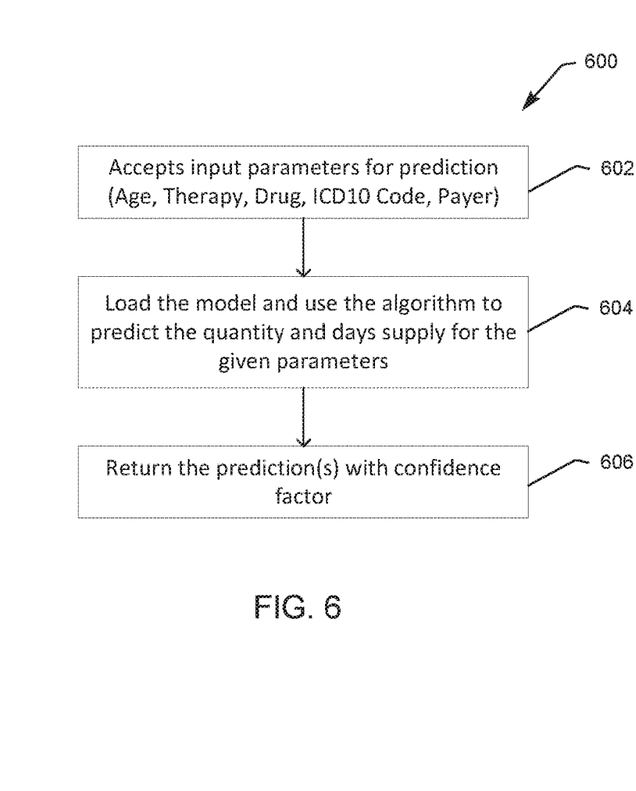
FIG. 6 is a block diagram of a flowchart illustrating methods for predicting required pharmacy element values in a prescription, according to an example embodiment.

FIG. 6 illustrates a method 600 for predicting required pharmacy element values in a prescription according to an example embodiment. The method 600 may be performed by the benefit manager device 102, partially by the benefit manager device 102 and partially by the pharmacy device 106, or may be otherwise performed. For the sake of simplicity, the benefit manager device 102 will be described as performing the steps of the method 600, but the embodiments described herein are not so limited.

Although not illustrated, several steps are usually performed before or simultaneously with the illustrated steps of the method 600. For example, a doctor faxes a handwritten prescription to a PBM or a pharmacy. When the PBM or pharmacy receives the faxed prescription, an intake team employee can enter in a patient name, a provider, and a prescribed drug into an intake form. The intake process can be performed by a human employee using conventional data entry methods. However, the intake team employee cannot enter RPE values because the intake team employee is not a pharmacist. After entering in the intake information, the intake team employee can pass the faxed prescription to a pharmacy team. The method 600 can assist the pharmacy team in filling faxed prescriptions.

The benefit manager device 102 can accept input parameters (i.e. factors) for predictions in step 602. In some embodiments, the input parameters can include patient age, drug therapy, prescribed drug, ICD 1 O code, and payer. According to an exemplary embodiment, the input parameters will apply to a machine learning algorithms used for prediction. Furthermore, the benefit manager device 102 can load one of the multiple machine learning algorithms to predict RPE elements in step 604. In some embodiments, the machine learning algorithm loaded can be the machine learning algorithm having the highest success rate, as determined in the method 500, described above. Furthermore, the benefit manager device 102 can generate a confidence value in the prediction of the RPE values in step 606.

Although not illustrated, the method 600 can further include the benefit manager device 102 pre-populating RPE values in a prescription filling form when the confidence value exceeds a threshold (e.g. 80% confidence value). The pre-populated value can be edited by a pharmacist if the prediction is incorrect.

Figure 7:
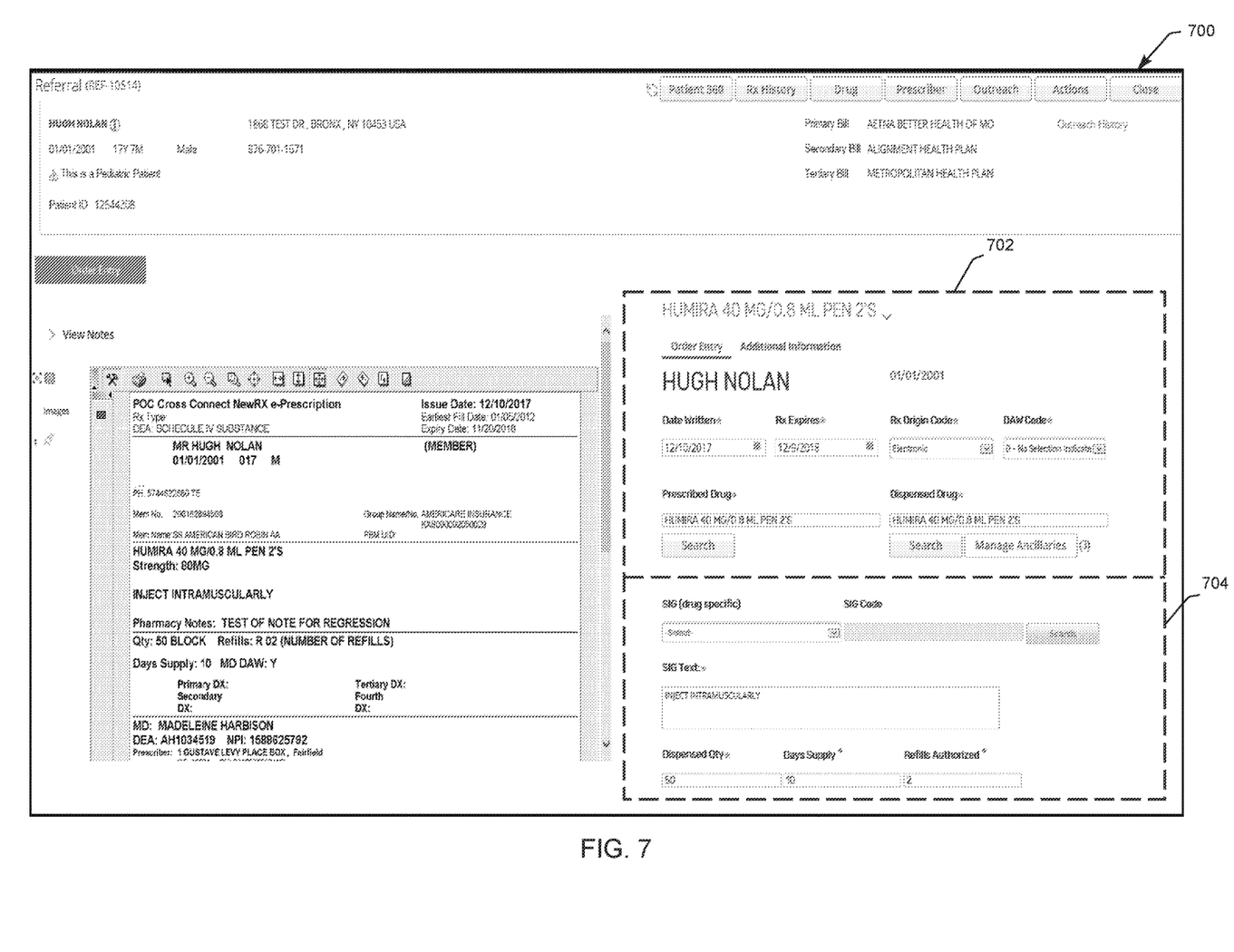
FIG. 7 is a screenshot illustrating an order entry screen with fields to be predicted using machine learning algorithms, according to an example embodiment.

FIG. 7 illustrates a prescription filling form 700 with pre-populated RPE values. As shown, the prescription filling form 700 can be displayed on a graphical user interface on a computer. Furthermore, the prescription filling form 700 can include intake information 702 and RPE information 704. Boxes in the intake information 702 section can be filled in by the intake team employee, or pulled from the intake form, and boxes of the RPE information 704 can be pre-populated by one of the multiple machine learning algorithms and reviewed by a pharmacist of pharmacist technician. As shown in FIG. 7, the RPE information 704 has been predicted accurately by the one of the multiple machine learning algorithms and pre-populated.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A Further, for information sent from element A to element B, element B may send requests for, or receipt acknowledgements of, the information to element A The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLU-ETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Example methods and systems for using machine learning algorithms are described. In the following description, for purposes of explanation, numerous specific details are set forth in order to provide a thorough understanding of example embodiments. It will be evident, however, to one of ordinary skill in the art that embodiments of the present disclosure may be practiced without these specific details.

What is claimed is:
1. A method comprising:
   identifying, by a machine learning algorithm selection subsystem implemented by a processor, one or more factors to be used by a machine learning algorithm in predicting a value of an element entered into a form;
   training, by the machine learning algorithm selection subsystem, the machine learning algorithm to predict the value of the element using a first subset of previously received data by analyzing known element values within the first subset of previously received data and a relationship between the known element values and the one or more factors;
   predicting, by the machine learning algorithm, respective known values of respective known elements for each of a second subset of previously received data, the second subset comprising a remainder of the previously received data not included within the first subset;
   evaluating, by the machine learning algorithm selection subsystem, a success rate for the machine learning algorithm at predicting respective known values of respective known elements for each of the second subset by determining whether the machine learning algorithm correctly predicted the respective known values of respective known elements for each of the second subset;
   receiving, by the machine learning algorithm, a new form subsequent to training and evaluating the machine learning algorithm;
   predicting, by the machine learning algorithm, the value of the element in the new form; and pre-populating, by the machine learning algorithm, the value of the element in the new form, as predicted.

2. The method of claim 1, wherein the machine learning algorithm comprises K-Neighbor, Random Forest, Gaussian Naive Bayes, and Stochastic gradient descent.

3. The method of claim 1, wherein the first subset contains 80% of the previously received data.

4. The method of claim 3, wherein the second subset contains the remaining 20% of the previously received data not included in the first subset.

5. The method of claim 1, further comprising:
a prediction subsystem determining a confidence value for predicting the value of the element in the new form.

6. The method of claim 5, further comprising:
the prediction subsystem determining whether the confidence value exceeds a threshold,
wherein the machine learning algorithm pre-populates the value of the element in the new form with the value of the element, as predicted, when the confidence value exceeds the threshold.

7. The method of claim 6, wherein the threshold is 80%.

8. A system comprising:
a storage device to store a machine learning algorithm;
a subsystem in communication with the storage device and configured to:
identify one or more factors to be used by a machine learning algorithm in predicting a value of an element entered into a form;
train the machine learning algorithm to predict the value of the element using a first subset of previously received data by analyzing known element values within the first subset of previously received data and a relationship between the known element values and the one or more factors;
predict respective known values of respective known elements for each of a second subset of previously received data, the second subset comprising a remainder of the previously received data not included within the first subset;
evaluate a success rate for the machine learning algorithm at predicting respective known values of respective known elements for each of the second subset by determining whether the machine learning algorithm correctly predicted the respective known values of respective known elements for each of the second subset;
a prediction subsystem configured to:
receive a new form subsequent to training and evaluating the machine learning algorithm;
predict the value of the element in the new form using the machine learning algorithm; and
pre-populate the value of the element in the new form, as predicted, by the machine learning algorithm.

9. The system of claim 8, wherein the machine learning algorithm comprises K-Neighbor, Random Forest, Gaussian Naive Bayes, and Stochastic gradient descent.

10. The system of claim 8, wherein the first subset contains 80% of the previously received data.

11. The system of claim 10, wherein the second subset contains a remaining 20% of the previously received data not included in the first subset.

12. The system of claim 8, wherein the subsystem at least includes a processor.

13. The system of claim 8, wherein the prediction subsystem is configured to determine a confidence value for predicting the value of the element in the new form.

14. The system of claim 13, wherein the prediction subsystem is further configured to determine whether the confidence value exceeds a threshold, wherein the prediction subsystem pre-populates the value of the element in the new form with the value of the element, as predicted, when the confidence value exceeds the threshold.

15. The system of claim 14, wherein the threshold is 80%.

16. A non-transitory machine-readable medium comprising instructions, which, when executed by one or more processors, cause the one or more processors to perform the following operations:
identify one or more factors to be used by a machine learning algorithm in predicting a value of an element entered into a form;
train the machine learning algorithm to predict the value of the element using a first subset of previously received data by analyzing known element values within the first subset of previously received data and a relationship between the known element values and the one or more factors;
predict respective known values of respective known elements for each of a second subset of previously received data, the second subset comprising a remainder of the previously received data not included within the first subset;
evaluate a success rate for the machine learning algorithm at predicting respective known values of respective known elements for each of the second subset by determining whether each of the machine learning algorithm correctly predicted the respective known values of respective known elements for each of the second subset;
receive a new form subsequent to training and evaluating the machine learning algorithm;
predict the value of the element in the new form using the machine learning algorithm; and
pre-populate the value of the element in the new form, as predicted, by the machine learning algorithm.

17. The non-transitory machine-readable medium of claim 16, wherein non-transitory machine-readable medium comprising instructions, which, when executed by the one or more processors, further cause the one or more processors to perform the following operations:
determine a confidence value for predicting the value of the element in the new form.

18. The non-transitory machine-readable medium of claim 17, wherein non-transitory machine-readable medium comprising instructions, which, when executed by the one or more processors, further cause the one or more processors to perform the following operations:
determine whether the confidence value exceeds a threshold, wherein the one or more processors pre-populates the value of the element in the new form with the value of the element, as predicted, when the confidence value exceeds the threshold.

19. The non-transitory machine-readable medium of claim 18, wherein the threshold is 80%.

20. The non-transitory machine-readable medium of claim 16, wherein the machine learning algorithm comprises at least one of K-Neighbor, Random Forest, Gaussian Naive Bayes, Stochastic gradient descent, or combinations thereof, and wherein the machine learning algorithm determines a confidence value for predicting the value of the element.

* * * * *